(12) United States Patent
Xu et al.

(10) Patent No.: US 7,514,531 B2
(45) Date of Patent: Apr. 7, 2009

(54) SPECIFIC BINDING SITES IN COLLAGEN FOR INTEGRINS AND USE THEREOF

(75) Inventors: Xuejun Xu, Missouri City, TX (US); Magnus Höök, Houston, TX (US); Jiyeun Kim, San Francisco, CA (US)

(73) Assignee: The Texas A&M University System, College Station, TX (US)

( * ) Notice: Subject to any disclaimer, the term of this patent is extended or adjusted under 35 U.S.C. 154(b) by 164 days.

(21) Appl. No.: 11/446,986

(22) Filed: Jun. 5, 2006

(65) Prior Publication Data
US 2007/0099244 A1    May 3, 2007

Related U.S. Application Data

(60) Provisional application No. 60/687,432, filed on Jun. 3, 2005.

(51) Int. Cl.
*A61K 38/04* (2006.01)
*G01N 33/53* (2006.01)

(52) U.S. Cl. .......................... 530/324; 530/330; 435/7.1
(58) Field of Classification Search ........................ None
See application file for complete search history.

(56) References Cited

U.S. PATENT DOCUMENTS 6,150,081 A * 11/2000 Van Heerde et al. ........ 430/569

FOREIGN PATENT DOCUMENTS

WO        WO 99/50281      * 10/1999

OTHER PUBLICATIONS

Siljander et al., Integrin activation state determines selectivity for novel recognition sites in fibrillar collagens. J Biol Chem. Nov. 12, 2004;279(46):47763-72.*
Lu X et al. Preferential antagonism of the interactions of the integrin alpha IIb beta 3 with immobilized glycoprotein ligands by snake-venom RGD (Arg-Gly-Asp) proteins. Evidence supporting a functional role for the amino acid residues flanking the tripeptide RGD in determining the inhibitory properties of snake-veno (1994) Biochem J 304: 929-936.*
Yokoyama and Ramakrishnan. Improved biological activity of a mutant endostatin containing a single amino-acid substitution. Br J Cancer. Apr. 19, 2004;90(8):1627-35.*
Aina et al. Therapeutic cancer targeting peptides. Biopolymers. 2002;66(3):184-99.*
Raynal, N.F. et al. *Mapping Cell Binding Using Collagen III "Toolkit": American Peptide Society*, 2005, vol. 19, pp. 431-432.
Raynal, N.F. et al. *Mapping Cell Binding Using Collagen III "Toolkit": American Peptide Symposium*, Jun. 10, 2005, vol. 80, No. 4, pp. 650.
Lahav, et al. *Enzymatically Catalyzed Disulfide Exchange is Required for Platelet Adhesion to Collagen Via Integrin $\alpha_2\beta_1$: Blood*, Sep. 15, 2003, vol. 102, No. 6, pp. 2085-2092.

* cited by examiner

*Primary Examiner*—Maher M Haddad
(74) *Attorney, Agent, or Firm*—Benjamin Aaron Adler

(57) ABSTRACT

The present invention identified a high affinity binding sequence in collagen type III for the collagen-binding integrin I domains. Provided herein are the methods used to characterize the sequence, the peptides comprising this novel sequence and the use of the peptides in enabling cell adhesion. Also provided herein are methods to identify specific integrin inhibitors, sequences of these inhibitors and their use in inhibiting pathophysiological conditions that may arise due to integrin-collagen interaction.

5 Claims, 8 Drawing Sheets

Fig. 1A
Fig. 1B
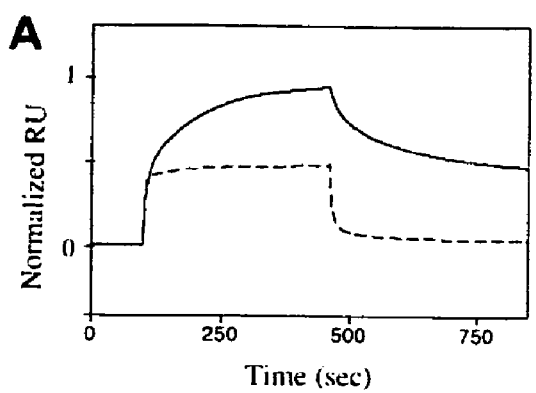
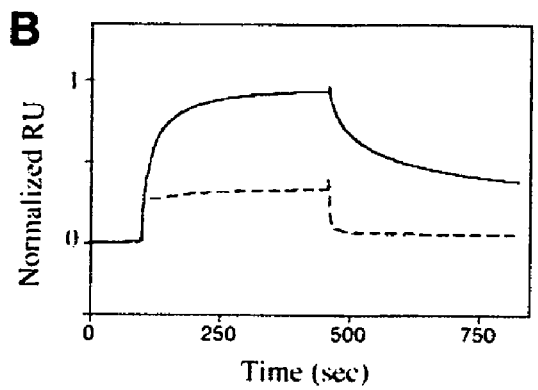
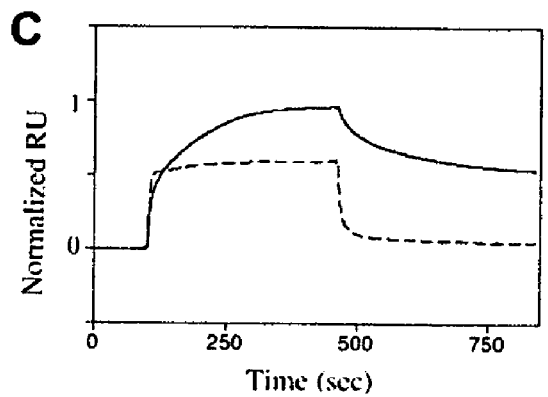
—— $\alpha_1 I$
--- $\alpha_2 I$
Fig. 1C
Fig. 2
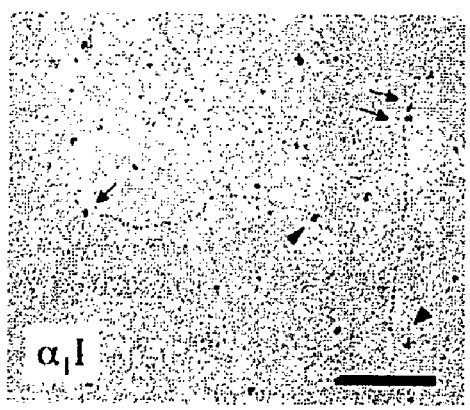
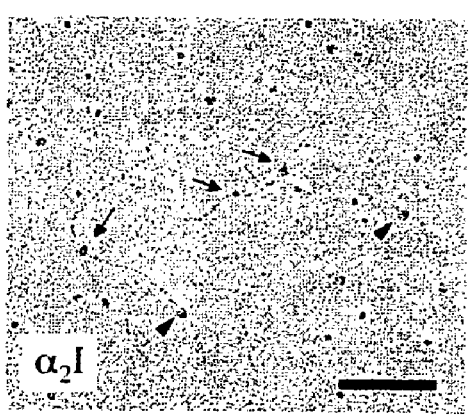

¹⁶¹ksgvavgglagypgpagvpgpagpogpogtsghogspgsogyqgpogeog
qagpsgpogpogaigpsgpaagkdgesGROGROGERGLOgpo
gikpagiogfpgmkghrgfdgrngekgetgaogikgenglogengao
gpmgprGAOGERGROGLOgaa³⁰⁷ SEQ ID NO: 18

1 : gpogpogpoGROGROGERGLOgpogpogpo SEQ ID NO: 15
2 : gpogpogpoGAOGERGROGLOgpogpogpo SEQ ID NO: 16
3 : gpogpogpoGPRGRTgpogpogpo SEQ ID NO: 17

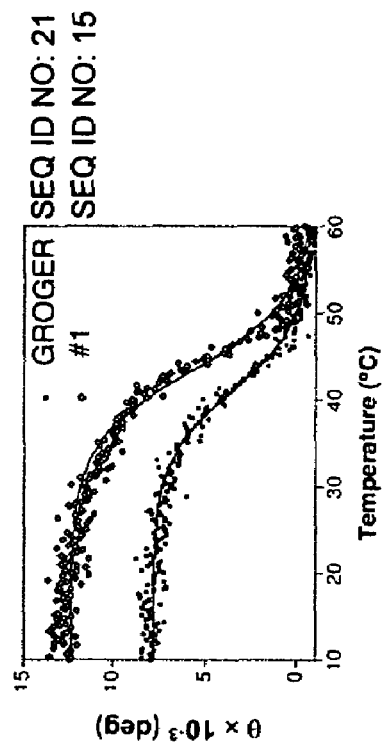
Fig. 8A
GFOGER : gpogpogpoGFOGERgpogpogpo
GLOGER : gpogpogpoGLOGERgpogpogpo
GROGER : gpogpogpoGROGERgpogpogpo
1 : gpogpogpoGROGROGERGLOgpogpogpo
SEQ ID NO: 19
SEQ ID NO: 20
SEQ ID NO: 21
SEQ ID NO: 15
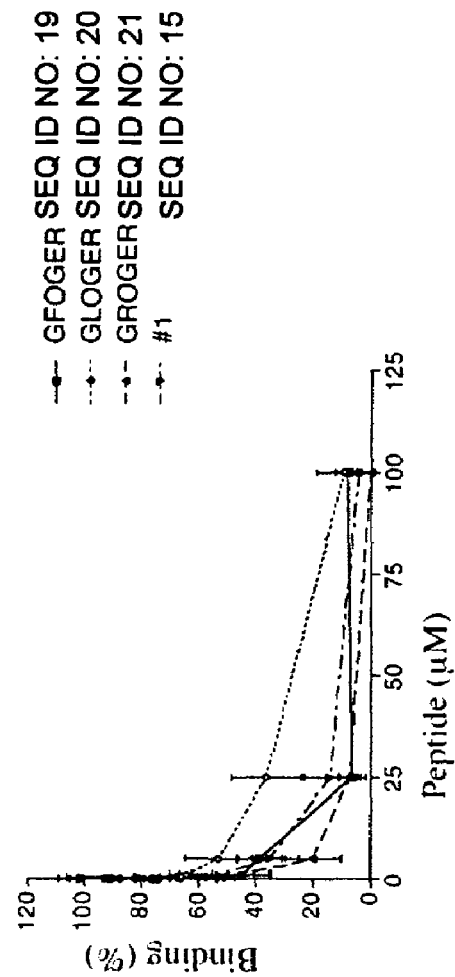
Fig. 8B
Fig. 8D
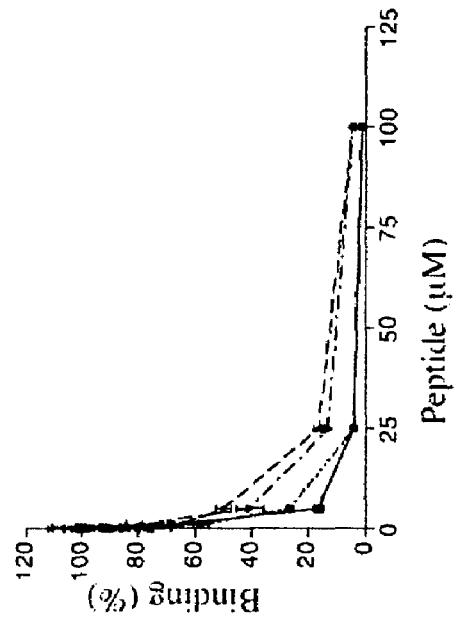
Fig. 8C

SPECIFIC BINDING SITES IN COLLAGEN FOR INTEGRINS AND USE THEREOF

CROSS REFERENCE TO RELATED APPLICATION

This non-provisional application claims benefit of provisional application U.S. Ser. No. 60/687,432 filed on Jun. 3, 2005, now abandoned.

FEDERAL FUNDING LEGEND

This invention was produced using funds obtained through grant AR44415 from the National Institutes of Health. Consequently, the federal government has certain rights in this invention.

BACKGROUND OF THE INVENTION

1. Field of the Invention

The present invention relates generally to the field of computer-aided molecular modeling and interaction of extracellular matrix protein with receptors and cell signaling. More specifically, the present invention relates to identification of motifs within the extracellular matrix protein, collagen type III that binds I domains of the integrins and designing of specific inhibitors that inhibit the interaction of the I domain of integrin with the collagen.

2. Description of the Related Art

Collagen is a major component of the extracellular matrix (ECM). At least 27 genetically different collagen types have been identified, each containing at least one dominant collagenous domain (Ramchandran, G. N., 1988). These collagenous domains have a characteristic triple helix structure formed by repeating Gly-X-Y sequences in each participating chain where X often is Proline and Y is hydroxyproline. The collagen monomers often assemble into more complex structures of varying organizations such as fibrils (types I-III, V and XI), networks (types IV, VIII and X) and beaded filaments (type VI) (Hulmes, D. J., 1992). The fibrillar collagen types I and III are the major structural components of the ECM of skin, cardiac and vascular tissues, whereas type II collagen is a major structural component of cartilage. In addition to contributing to the structural integrity of the tissues, collagens also affect cell behaviour through interactions with other matrix proteins and cellular receptors (Prockop, D. J. and Kivirikko, 1995; Kuivaniemi, H., et al., 1997; Gelse, K. et. al., 2003; Myllyharju, J. and Kivirikko, K. I., 2001).

The integrins are a family of heterodimeric cell surface receptors involved in cell-cell and cell-substrate adhesion. They act as bridging molecules that link intracellular signaling molecules to the ECM through bi-directional signaling and control cell behaviour and tissue architecture (Hynes, R. O., 1992). Four integrins, $\alpha_1\beta_1$, $\alpha_2\beta_1$, $\alpha_{10}\beta_1$ and $\alpha_{11}\beta_1$ have been shown to bind collagens (Kramer, R. H. and Marks, N., 1989; Camper, L. et al., 1998; Velling, T. et al., 1999). Of these, the $\alpha_1\beta_1$ and $\alpha_2\beta_1$ integrins have been studied In more detail compared to the others. Collagen integrin interactions play a role in normal and pathological physiology and directly affect cell adhesion, migration, proliferation and differentiation as well as angiogenesis, platelet aggregation and ECM assembly (Gulberg and Lundgren-Akerlund, 2002). However, the precise molecular mechanisms that lead to these activities are not understood.

Collagen binding by the four integrins is mediated by a ~200 amino acids long so-called inserted domain (I domain) found between blades 2 and 3 of the β-propeller domain of the α chains. All four I domains ($\alpha_1$I, $\alpha_2$I, $\alpha_{10}$I, $\alpha_{11}$I) contain a metal ion-dependent adhesion site (MIDAS) that is required for coordinating a divalent cation and is essential for collagen binding. Synthetic collagen peptides containing the type I collagen derived sequences, GFOGER (SEQ ID NO: 1) or GLOGER (SEQ ID NO: 2) have been reported to bind with high affinity to $\alpha_1$I, $\alpha_2$I and $\alpha_{11}$I; furthermore, synthetic peptides containing these sequences inhibit the binding of I domains to intact collagens (Knight, C. G. et al., 1998; Zhang, W. M. et al., 2003; Siljander, P. R. et al., 2004). The crystal structures of apo-$\alpha_2$I and $\alpha_2$I in complex with a collagen peptide containing the GFOGER (SEQ ID NO: 1) sequence have been solved (Emsley, J. et al., 2000) and showed that the apo-$\alpha_2$I adopted an inactive "closed" conformation and the ligand bound $\alpha_2$I, an active "open" conformation (Lee, J. O. et al., 1995). The Glu residue in the collagen peptide was shown in the structure of the complex to directly interact with a $Mg^{2+}$ ion coordinated by the MIDAS motif and the Arg residue forms a salt bridge with $D_{219}$ in $\alpha_2$I. The importance of the GER sequence in collagen for integrin binding was confirmed by mutagenesis studies, which showed that replacing Glu in the collagen peptide with an Asp residue completely abolished the binding whereas replacing the Arg with a Lys residue reduced the binding by 50% (Knight, C. G. et al., 2000). The Phe residue in the collagen sequence appeared to participate in hydrophobic interactions with $\alpha_2$I and could be replaced by Leu. Both GFOGER (SEQ ID NO: 1) and GLOGER (SEQ ID NO: 2) bind to $\alpha_1$I and $\alpha_2$I (Xu, Y. et al., 2000). However, changing the Phe residue to a Met or an Ala reduced the apparent affinity of I domains (Siljander, P. R. et al., 2004). GASGER (SEQ ID NO: 3) was also reported to be recognized by the I domains but bound with lower affinity than GFOGER (SEQ ID NO: 1) and GLOGER (SEQ ID NO: 2) (Zhang, W. M. et al., 2003; Siljander, P. R. et al., 2004; Xu, Y. et al., 2000). Therefore, GFOGER (SEQ ID NO: 1) and GLOGER (SEQ ID NO: 2) are the only two known collagen-derived sequence motifs that support high affinity binding by the collagen-binding I domains. However, the GFOGER (SEQ ID NO: 1) and GLOGER (SEQ ID NO: 2) motifs are absent in some collagens such as human type III collagen. Additionally, previous studies have shown that CHO cell expressing $\alpha_1\beta_1$ and $\alpha_2\beta_1$ could adhere and spread on human type III collagen and furthermore, the recombinant proteins of $\alpha_1$I and $\alpha_2$I could bind to this collagen type (Nykvist, P. et al., 2000)

Thus, there is a need in the art for understanding the mechanism by which type III collagen binds to integrins and in designing of integrin specific inhibitors. The present invention fulfills this long-standing need and desire in the art.

SUMMARY OF THE INVENTION

The present invention is directed to a binding motif for collagen binding I domains comprising amino acid sequence GROGER (SEQ ID NO: 4). The present invention is further directed to a method of identifying an inhibitor of integrin-collagen interaction. Such a method comprises designing a test compound comprising a sequence that is specifically recognized by the I domain of the integrin, wherein said design is based on computer-aided molecular modeling. Further, the level of binding of the integrin to the collagen is compared in the presence or absence of the test compound, where a decrease in binding of the integrin to the collagen in presence of the test compound indicates that the test compound is the inhibitor of the integrin-collagen interaction.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIGS. 1A-C show the analyses of the binding of $\alpha_1 I$ and $\alpha_2 I$ to fibrillar collagen type I-III by SPR. Representative profiles of the relative SPR responses of the binding of 1 µM $\alpha_1 I$ and $\alpha_2 I$ to immobilized type I procollagen is shown in FIG. 1A, type II mature collagen is shown in FIG. 1B and type III procollagen is shown in FIG. 1C in the presence of 1 mM MgCl2. Responses to blank cells were subtracted. Y axis values are RUs normalized to the maximum RUs of all binding to type I-III collagens, respectively FIG. 2 shows electron micrographs of human type III procollagen in complex with $\alpha_1 I$ or $\alpha_2 I$ following rotary shadowing. The C-terminal propeptide of type III collagen, indicated by arrowheads, appeared as a knob at one end of each of the collagen molecules. Bound $\alpha_1 I$ and $\alpha_2 I$, indicated by arrows, appeared as beads along the collagen strands. The scale bars indicate 100 nm.

FIG. 4A shows the amino acid sequence (SEQ ID NO: 18) of the high affinity binding region corresponding to 270-300 nm from the C-terminal propeptide, indicated by underlined letters, and its flanking area in human type III collagen. Residues around the GER motif are indicated by upper case letters. FIG. 4B shows the amino acid sequences of the synthetic collagen peptides. Human type III collagen specific sequences are indicated by underlined and upper case letters, and type I collagen specific sequences are indicated by upper case letters. Three GPO triplets are included on either side to ensure the formation of triple helices. FIG. 4C shows circular dichroism spectra of the synthetic collagen peptides. Peptides #1, #2 and #3 in FIGS. 4B and 4C are identified as SEQ ID NO: 15, 16 and 17, respectively.

FIGS. 8A-D show analyses of GROGER (SEQ ID NO: 4) as the minimal binding sequence for $\alpha_1 I$ and $\alpha_2 I$. FIG. 8A shows the amino acid sequences of the synthetic collagen peptides (SEQ ID NOs: 19, 20, 21, 15). Three GPO triplets are included on either side to ensure the formation of triple helices. FIG. 8B shows temperature-dependent denaturation profiles of synthetic collagen peptides. Ellipticity at 225 nm was measured as temperature increased from 10 to 50° C. at the rate of 20° C./hr. Melting points of peptides were calculated by nonlinear fitting using the Boltzmann sigmoidal equation (GraphPad Prism). FIGS. 8C and 8D show inhibition of the binding of $\alpha_1 I$ and $\alpha_2 I$ to type III collagen by synthetic collagen peptides. Different concentrations of peptides were mixed with 0.5 µM $\alpha_1 I$ (FIG. 8C) and 5 µM $\alpha_2 I$ (FIG. 8D) before being added to microtiter wells coated with human mature type III collagen (FibroGen). The binding in the absence of peptide was set to 100%. Data were presented as the mean value±S.E. of A405 nm (n=3) from a representative experiment.

Figures 10A, 10B, 10C, 10D:
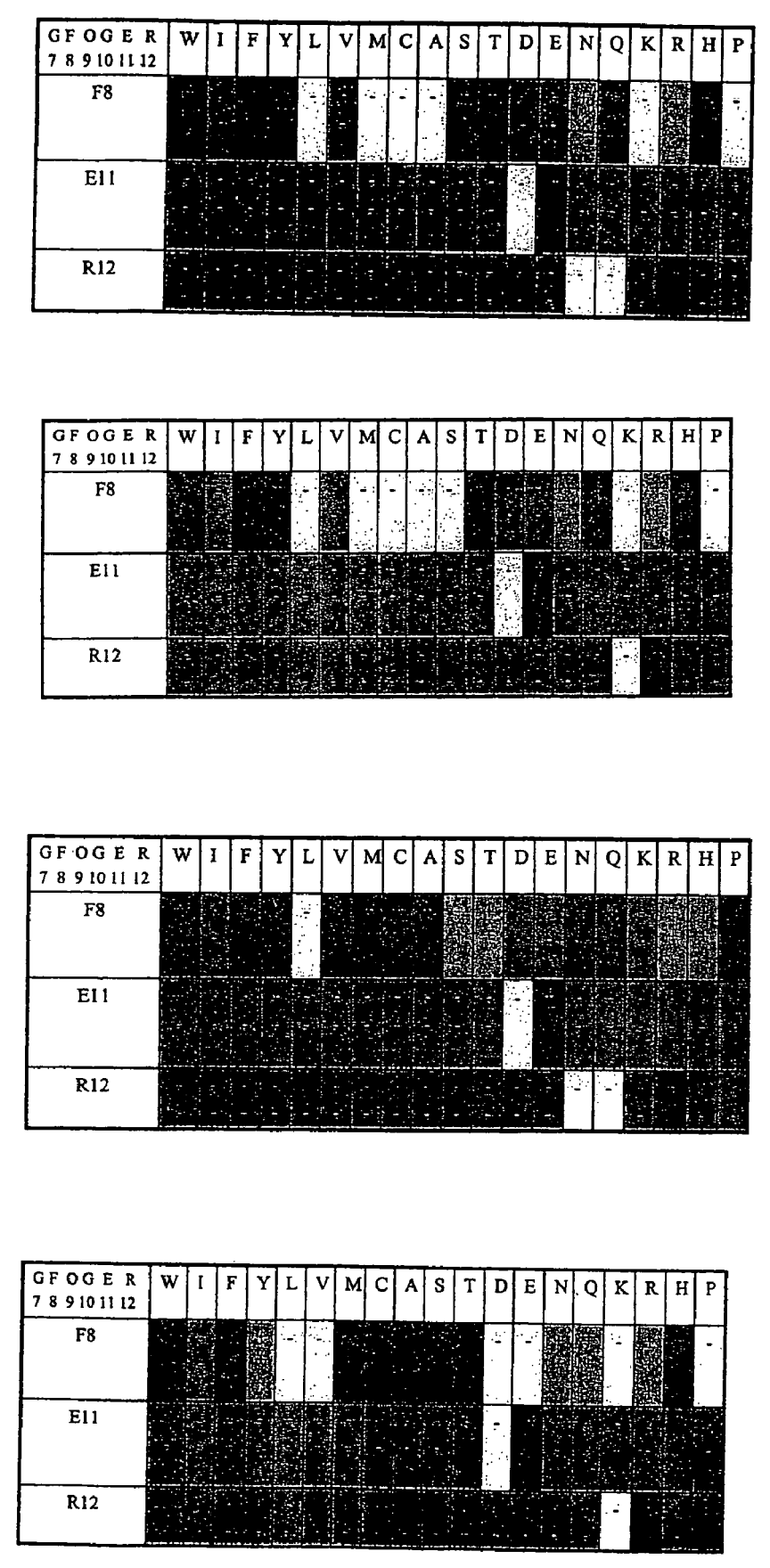

FIGS. 10A-D are computer modeling profiles showing specificity of collagen sequence to different I domains of collagen binding integrin alpha subunits. Computational prediction of I domain-collagen peptide complex used X-ray crystal structure of $\alpha_2 I$ domain with collagen peptide, GFOGER (SEQ ID NO: 1) as template. FIG. 10A shows the alpha-1 I domain in complex with collagen peptide. FIG. 10B shows the alpha-2 I domain in complex with collagen peptide. FIG. 10C shows alpha-10 I domain in complex with collagen peptide. FIG. 10D shows alpha-11 I domain in complex with collagen peptide.

Figure 3:
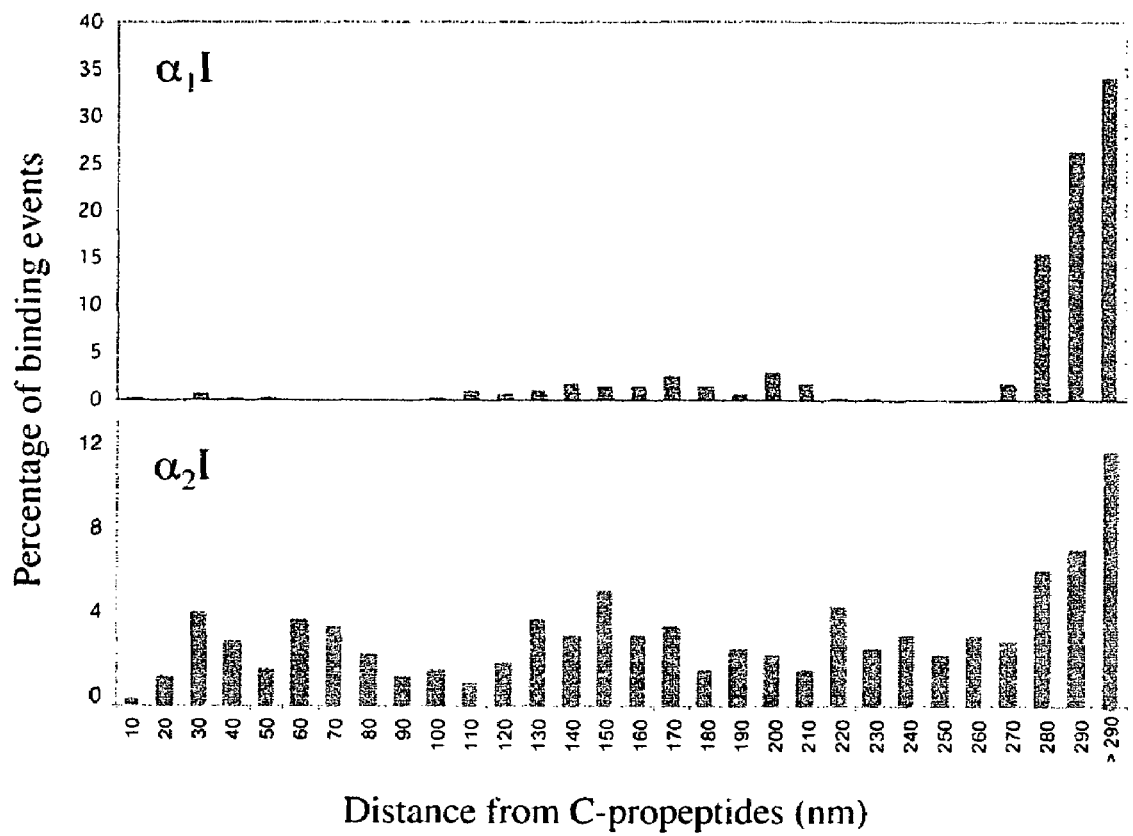
FIG. 3 shows histograms of the binding events of $\alpha_1 I$ and $\alpha_2 I$ along human type III procollagen. The events were binned every 10 nm, and the percentages of the binding events in each 10 nm bin over the total binding events counted are given. For $\alpha_1 I$, a total of 269 binding events were counted, and for $\alpha_2 I$, a total of 299 events were counted.

The binding affinities is shown as follows: + represents binding affinity close to the template (blue), ++ represents slightly higher binding affinity (green), +++ represents much higher binding affinity (dark green), – represents lower binding affinity (yellow) and −− represents disrupted binding affinity (red). In the computational mutation in a collagen peptide, F8 on middle and trailing strand were substituted simultaneously, E11 on middle strand was replaced for each mutation simulation and R12 on middle and trailing strand were substituted simultaneously for each mutation simulation.

DETAILED DESCRIPTION OF THE INVENTION

The present invention identified a novel sequence motif, GROGER (SEQ ID NO: 4) from human type III collagen and characterized its binding to the I domains of integrins $\alpha_1$ and $\alpha_2$. Briefly, the binding of recombinant I domains from integrins $\alpha_1$ and $\alpha_2$ ($\alpha_1 I$ and $\alpha_2 I$) to fibrillar collagens types I-III was characterized and it was observed that each I domain bound to the three types of collagen with similar affinities. Using rotary shadowing followed by electron microscopy, a high affinity binding region was identified in the human type III collagen that was recognized by $\alpha_1 I$ and $\alpha_2 I$. Examination of the region further revealed the presence of two sequences that contained the critical GER motifs, GROGER (SEQ ID NO: 4) and GAOGER (SEQ ID NO: 5). Synthetic collagen-like peptides containing these two motifs were synthesized and their triple helical nature was confirmed by circular dichroism spectroscopy.

Further, it was demonstrated that the GROGER (SEQ ID NO: 4)-containing peptides were able to bind to both $\alpha_1 I$ and $\alpha_2 I$ with high affinity and effectively inhibit the binding of $\alpha_1 I$ and $\alpha_2 I$ to type III and type I collagens, whereas the GAOGER (SEQ ID NO: 5)-containing peptide was considerably less effective. Furthermore, the GROGER (SEQ ID NO: 4)-containing peptide supported adhesion of human lung fibroblast cells when coated on a culture dish. Additionally, the present invention also disclosed the use of computer-aided molecular modeling to identify sequences that are specifically recognized by individual I domains on the integrins. Thus, the finding of the present invention helps to understand the molecular interactions between collagens and integrins. It is further contemplated to synthesize peptides comprising the specific sequences identified by the modeling approach and test their utility in inhibiting integrin-collagen interaction and affect the biological and pathological conditions that arise due to such interaction.

Type III collagen is a homotrimeric molecule and is a member of the fibrillar collagen family. It co-localizes with type I collagen in tissues such as blood vessels and skin and plays a role in the development of these tissues (Prockop, D. J and Kivirikko, K. I., 1995; Liu, X et al., 1997). In vitro, it has been reported that the type III collagen was able to support adhesion and spreading of cells expressing integrin $\alpha_1 \beta_1$ or $\alpha_2 \beta_1$ (Nykvist, P. et al., 2000). However, human type III collagen does not contain the two previously known high affinity integrin-binding motifs, GFOGER (SEQ ID NO: 1) and GLOGER (SEQ Id NO: 2). The present invention compared the binding of $\alpha_1 I$ and $\alpha_2 I$ to the three different types of fibrillar collagen (types I, II and III). Surface plasmon resonance (SPR) analysis showed that all three collagen types contained at least two classes of binding sies for the two I domains. A high affinity integrin-binding site was located by rotary shadowing of I domains in complex with type III procollagen and a synthetic collagen triple helix peptide containing the GROGER (SEQ ID NO: 4) sequence was shown to bind with high affinity to the I domains and could serve as a substrate for integrin-dependent cell adhesion. Other I domain-binding sites in type III collagen indicated by the rotary shadowing experiment might represent low affinity sites.

Recently, the role of hydrophobic residues at the second position in GFOGER (SEQ ID NO: 1) and GLOGER (SEQ ID NO: 2) sequences was studied, and the interactions between $\alpha_2 I$ and a number of GER-containing collagen peptides comprising 6 amino acids with Glycine as the first amino acid and differing only in the second or the third position from GLOGER (SEQ ID NO: 2) or GFOGER (SEQ ID NO: 1) was examined (Siljander et al., 2004). It was observed that with respect to the second position, the order of the inhibition potency was $F \geqq L \geqq M > A$. All these residues were hydrophobic or non-polar. However, the GROGER (SEQ ID NO: 4) sequence identified in this invention contains a charged residue at the second position. Furthermore, using the peptide inhibition assay to compare the apparent affinity of GROGER (SEQ ID NO: 4) to integrin I domains with that of GFOGER (SEQ ID NO: 1) and GLOGER (SEQ ID NO: 2), the present invention demonstrated that GROGER exhibited a somewhat higher affinity than GFOGER (SEQ ID NO: 1) and GLOGER (SEQ ID NO: 2) for $\alpha_2 I$ and slightly lower affinity for $\alpha_1 I$. These observation might suggest that different integrins recognise different sites in collagen with different affinities.

Furthermore, to investigate how the presence of a charged residue would affect the interactions with the I domains, computer modeling was performed based on the published structure of $\alpha_2 I$ in complex of a GFOGER(SEQ ID NO: 1)-containing collagen peptide. Interestingly, the change from Phe (F) to Arg (R) did not affect the positions of neighboring amino acid residues in $\alpha_2 I$. An additional hydrogen bond interaction was observed between the Arg (R) residue and the carbonyl backbone of $Gln^{215}$ in $\alpha_2 I$. This additional contact might explain the slightly higher observed affinity of $\alpha_2 I$ for GROGER (SEQ ID NO: 4) compared with GLOGER (SEQ ID NO: 2). Whether this change affected the downstream signaling events by integrins was not clear.

A search of different collagen sequences for the presence of GROGER (SEQ ID NO: 4) indicated that it was present in a variety of collagen types (Table 1). Noticeably, it was present in all the type I collagens examined, yet, this sequence was not identified as a high affinity binding sequence in previous studies with type I collagen (Xu, Y. et al., 2000). A more detailed examination revealed that it was only present in the $\alpha_2 I$ chain of type I collagens from bovine or chicken, which were the sources of type I collagens in the previous studies. As type I collagen is composed of two $\alpha_1$ chains and one $\alpha_2$ chain, the presence of GROGER (SEQ ID NO: 4) in the $\alpha_2$ chain might not provide sufficient interactions with residues in the I domains to allow a high affinity binding. However, it would be interesting to examine whether this motif mediates a high affinity interactions between the collagen-binding I domains and type of collagen from human, mouse or dog is interesting.

TABLE 1

The presence of GROGER (SEQ ID NO: 4) sequence in different types of collagen.

| Species | Type of collagen | α chain | Position of the starting Gly |
|---|---|---|---|
| Human | Type I | $\alpha_1$ (I) | 239 |
|  |  | $\alpha_2$ (I) | 151 |
|  | Type III | $\alpha_1$ (III) | 237 |
|  | Type VII | $\alpha_1$ (VII) | 2055 |
|  | Type X | $\alpha_1$ (X) | 197 |
| Mouse | Type I | $\alpha_1$ (I) | 228 |
|  |  | $\alpha_2$ (I) | 157 |
|  | Type III | $\alpha_1$ (III) | 236 |
|  | Type X | $\alpha_1$ (X) | 197 |
| Dog | Type I | $\alpha_1$ (I) | 235 |
|  |  | $\alpha_2$ (I) | 151 |
| Chicken | Type I | $\alpha_2$ (I) | 150 |
|  | Type XIV | $\alpha_1$ (XIV) | 1697 |
| Rat | Type I | $\alpha_2$ (I) | 157 |
| Bovine | Type I | $\alpha_2$ (I) | 149 |
| Bullfrog | Type I | $\alpha_2$ (I) | 142 |

The present invention also contemplates using a computer-aided molecular modeling approach to identify sequences that are specifically recognized by individual I domains on the integrins and thus can be used as base for developing integrin specific inhibitors. Such sequences can also be used to design specific binding sites in recombinant collagen or collagen-like proteins and to synthesize peptides that could be used as inhibitors of integrin-collagen interaction.

In one embodiment of the present invention, there is provided a binding motif for collagen-binding I domains comprising an amino acid sequence GROGER (SEQ ID NO: 4). The I domains of integrins bound by such a motif include but may not be limited to $\alpha_1$ and $\alpha_2$ integrins. Moreover, the motif may comprise a charged amino acid in second position. Generally, the charged amino acid may form a hydrogen bond with carbonyl background of gluatmine at position 215 in $\alpha_2$I. Specifically, the charged amino acid may be arginine. Further, the motif may be present on N-terminal of human type III collagen or in the $\alpha_1$ and $\alpha_2$ chain of human type I collagen.

In a related embodiment of the present invention, there is provided a recombinant collagen or collagen like protein comprising the binding motif described supra. Such a recombinant collagen or collagen-like protein may have sequence of SEQ ID NO: 15 or SEQ ID NO: 21. In a further related embodiment of the present invention, there is provided an expression vector. Such an expression vector may comprise a DNA sequence encoding the recombinant collagen or collagen-like protein described earlier. In a still further related embodiment of the present invention, there is provided a host cell comprising and expressing the expression vector described earlier.

In another embodiment of the present invention, there is provided a synthetic collagen or collagen-like peptide comprising the binding motif described supra. Although not limited to, such a peptide may have sequence of SEQ ID NO: 15 or SEQ ID NO: 21. Generally, such a peptide has a triple helical structure. Further, such a synthetic peptide may bind I domains of integrins $\alpha_1$ and $\alpha_2$. In yet another embodiment of the present invention, there is provided a method of identifying an inhibitor of an integrin-collagen interaction, comprising: designing a test compound comprising a sequence that is specifically recognized by the I domain of the integrin, where the design is based on computer-aided molecular modeling, and comparing the level of binding of the integrin to the collagen in the presence or absence of the test compound, where a decrease in binding of the integrin to the collagen in presence of the test compound indicates that the test compound is the inhibitor of the integrin-collagen interaction. The examples of integrin that are bound by such inhibitors may not be limited to but include $\alpha_1\beta_1$, $\alpha_2\beta_1$, $\alpha_{10}\beta_1$ or $\alpha_{11}\beta_1$. The collagen whose interaction with the integrin is affected may be a type I, II or III collagen. Further, the inhibitor has a triple helical structure and may comprise an amino acid sequence including but not limited to GFPGER (SEQ ID NO: 6), GFOGEN (SEQ ID NO: 7), GFOGEK (SEQ ID NO: 8), GNOGER (SEQ ID NO: 9), GSOGER (SEQ ID NO: 10), GVOGER (SEQ ID NO: 11) or GPOGER (SEQ ID NO: 12).

In a related embodiment of the present invention, there is provided an inhibitory compound that is identified by the method described above. In a further related embodiment of the present invention, there is provided a recombinant collagen or collagen-like protein comprising the inhibitory sequence indentified by the method described supra. In a still further related embodiment of the present invention, there is provided an expression vector, comprising a DNA sequence encoding the recombinant collagen or collagen-like protein described supra. In another related embodiment of the present invention, there is provided a host cell comprising and expressing the expression vector described earlier.

In a further related embodiment of the present invention, there is provided a synthetic collagen or collagen-like peptide comprising the inhibitory sequence identified by the method described supra. Further, the inhibitory sequence in a triple helical structure may not be limited to but includes GFPGER (SEQ ID NO: 6), GFOGEN (SEQ ID NO: 7), GFOGEK (SEQ ID NO: 8), GNOGER (SEQ ID NO: 9), GSOGER (SEQ ID NO: 10), GVOGER (SEQ ID NO: 11) or GPOGER (SEQ ID NO: 12). Examples of integrins that are bound by such peptides are the same as discussed earlier.

In another embodiment of the present invention, there is provided a method of inhibiting integrin-collagen interaction, comprising: contacting a sample comprising the integrin and the collagen with the peptide discussed supra, where the peptide binds the integrin with a greater affinity than the collagen, thereby inhibiting the integrin-collagen interaction. Examples of biological processes contributed by integrin-collagen interaction and may be affected by the peptide may not be limited to but include cell adhesion, cell migration, cell proliferation, cell differentiation, angiogenesis, platelet aggregation or extracellular matrix assembly. In a still further related embodiment of the present invention, there is provided a pharmaceutical composition comprising the inhibitory compound identified by the method described supra and a pharmaceutically acceptable carrier.

In yet another embodiment of the present invention, there is provided a method of treating an individual having a pathophysiological condition resulting from integrin-collagen interaction, comprising the step of administering to the individual a pharmacologically effective amount of the composition discussed supra, such that the composition inhibits the integrin-collagen interaction, thereby treating the individual having the pathophysiological condition. Examples of the pathophysiological conditions are may not be limited to but include inflammation, tumor growth, metastasis or angiogenesis.

As used herein, the term "compound" or "inhibitor" or "inhibitory compound" means a molecular entity of natural, semi-synthetic or synthetic origin that blocks, stops, inhibits, and/or suppresses integrin interactions with collagen.

As used herein, the term "contacting" refers to any suitable method of bringing integrin, collagen and the inhibitory compound, as described, or a cell comprising the same and the inhibitory compound. In vitro or ex vivo this is achieved by exposing the integrin, collagen to the inhibitory compound or cells comprising the same to the compound or inhibitory agent in a suitable medium. For in vivo applications, any known method of administration is suitable as described herein.

The following example(s) are given for the purpose of illustrating various embodiments of the invention and are not meant to limit the present invention in any fashion.

EXAMPLE 1

Recombinant I Domains

Recombinant I domains of integrin $\alpha 1$ and $\alpha_2$ subunits were generated and isolated as (Xu, Y et al., 2000; Rich, R. L. et al., 1999). Purified recombinant proteins were examined by SDS-polyacrylamide gel electrophoresis (PAGE) followed by staining with Coomassie blue.

EXAMPLE 2

Purification of Recombinant Procollagen

Frozen yeast cells expressing recombinant type I and III procollagens were obtained from FibroGen, Inc (San Francisco, Calif.). The yeast cells expressed both genes encoding human collagen and prolyl 4-hydroxylase enabling formation of hydroxyproline residues and thermally stable triple helical collagen. The cells were thawed in an ambient-temperature water bath and resuspended in a Start buffer (0.1 M Tris, 0.4 M NaCl, 25 mM EDTA, 1 mM phenylmethylsulfonyl fluoride (PMSF), 1 mM pepstatin, pH 7.5). The cells were lysed using a French press, and the lysate was centrifuged at 30,000×g for 30 min at 4° C. The supernatant was filtered through a 0.45-mm membrane, and the pH of the filtrate was adjusted to 7.5. An affinity column was prepared by coupling a recombinant collagen-binding MSCRAMM from *Staphylococcus aureus* (Patti et al., 1992) to CNBr-activated Sepharose 4B (Amersham Biosciences). The supernatant was applied to the column and incubated overnight at 4° C. The column was washed with the Start buffer and bound material was eluted with 0.5 M acetic acid. Fractions were examined by SDS-PAGE (4%/8%) under reducing conditions followed by Coomassie blue staining. Fractions with procollagen were pooled. The concentration of the procollagen was estimated by comparing its band intensity with that of known amount of type I collagen (Vitrogen) in Coomassie blue stained SDS-gels.

EXAMPLE 3

Surface Plasmon Resonance (SPR) Measurements

For the analyses of interactions between recombinant I domains and fibrillar collagens, SPR measurements were carried out at ambient temperature using the BIAcore 3000 system (BIAcore, Uppsala, Sweden) as described previously (Rich et al., 1999) with following modifications. First, purified recombinant human procollagens I and III (described above), or bovine mature type II collagen (Sigma) were immobilized on the flow cells of a CM5 chip resulting in 200-700 response units of immobilized protein. Different concentration of the $\alpha_1 I$ and $\alpha_2 I$ proteins in HBS buffer (25 mM HEPES, 150 mM NaCl, pH 7.4) containing 5 mM β-mercaptoethanol, 1 mM MgCl2, and 0.05% octyl-D-glucopyranoside were passed over the immobilized collagen at 30 µl/min for 4 min. Regeneration of the collagen surfaces was achieved with 20 µl of HBS containing 0.01% SDS.

Binding of $\alpha_1 I$ and $\alpha_2 I$ to a reference flow cell, which had been activated and deactivated without the coupling of collagen, was also measured and subtracted from the response to collagen-coated flow cells. SPR sensorgrams from different injections were overlaid using the BIAevaluation software (BIAcore AB). Data from the steady state portion of the sensorgrams were used to determine the binding affinities. Based on the correlation between the SPR response and change in protein mass on the surfaces of flow cells, values for the binding ratio, $v_{bound}$, and the concentration of free protein, $[P]_{free}$, were calculated using the equations described previously (Rich, R. L. et al., 1999). Scatchard analysis was performed by plotting $v_{bound}/[P]_{free}$ against $v_{bound}$ in which the negative reciprocal of the slope is the dissociation constant, $K_D$. Nonlinear regression was also performed by plotting $v_{bound}$ against $[P]_{free}$ and fitted with the one-binding class or the two-binding class models using the GraphPad Prism™ software (GraphPad Software Inc., San Diego, Calif.). Results from the two models were compared with respect to the value of $R^2$ and the degree of freedom of the curve fit. The model that gave $K_D$ values outside the experimental data range was excluded. Experimental results were reproducible with at least three independent protein preparations.

SPR measurements for the analyses of the interactions between I domains and synthetic collagen peptides were carried out at 15° C. using the BIAcore 3000 system. The synthetic collagen peptide was immobilized onto a flow cell of a CM5 chip and various concentrations of recombinant I domains were passed over the coated surface at 50 µl/min. Responses on a reference flow cell were substracted from responses of the peptide-coated flow cell. The BIAevaluation 3.0 software was used to determine the association and dissociation rates ($k_{on}$ and $k_{off}$), and $K_D$ with a 1:1 binding model. $R_{max}$ of fitting was similar to calculated $R_{max}$. The Chi$^2$ of each fitting was less than 2.

EXAMPLE 4

Competition Enzyme-linked Immunosorbent Assay (ELISA)

Microtiter wells (Immulon 4, Thermo Labsystems) were coated with 1 µg of mature bovine type I collagen (Vitrogen) or purified human type III procollagen in HBS for 2 hrs at room temperature. The wells were washed with HBS and incubated with a blocking buffer (HBS containing 0.1% w/v ovalbumin and 0.05% v/v Tween 20) overnight at 4° C. Varying concentrations of peptides were mixed with fixed concentrations of recombinant I domains in the blocking buffer containing 1 mM MgCl2 and 5 mM β-mercaptoethanol and then added to the wells. After incubation at 4° C. for 3 hrs with gentle shaking, the wells were extensively washed with HBS containing 0.05% Tween 20 and 1 mM MgCl2. Bound $\alpha_1 I$ or $\alpha_2 I$ was detected by incubation with an anti-His monoclonal antibody (Amersham Bioscience) diluted 1:3000 in the blocking buffer containing 1 mM MgCl2 for 1 hr at room temperature, followed by incubation with goat anti-mouse IgG (H+L)-alkaline phosphatase conjugate (Bio-Rad) (1:3000 dilution in the blocking buffer 1 mM MgCl2) for 1 hr at room temperature. Bound antibodies were quantified by adding 100 µl of 1.3 M diethanolamine, pH 9.8, containing 1 mM $MgCl_2$, and 1 mg/ml p-nitrophenyl phosphate (Southern Biotechnology Associates, Birmingham, Ala.) to each well. The absorbance at 405 nm (A405 nm) was measured after 20-40 min of incubation at room temperature. Background binding to the wells was determined by incubating the I domains in wells that had been treated with blocking buffer alone. These values were subtracted from the values generated in the collagen-coated wells to determine collagen-specific binding. Data were presented as the mean value±S.E. of $A_{405\ nm}$ (n=3).

EXAMPLE 5

Rotary Shadowing and Electron Microscopy

Rotary shadowing and electron microscopy of I domain-collagen complexes were performed as described previously (Xu, Y et al., 2000). Each binding event was measured from the C-terminal end of type III collagen, that is from the base of the globular domain, and to the middle of the binding spot. The binding events were then binned for every 10 nm along the collagen strand. The percentage of the number of events in each bin over total events counted was calculated and plotted against the length of the collagen strand.

EXAMPLE 6

Synthesis and Purification of Collagen Peptides

Peptides were synthesized by a solid phase method on a TentaGel R RAM resin (RAPP Polymere GmbH, Tubingen, Germany) using Fmoc chemistry and a model 396 MBS Multiple Peptide Synthesizer from Advanced ChemTech Inc. (Louisville, Ky.). Fmoc amino acids were purchased from Novabiochem, San Diego, Calif. Coupling of amino acids was carried out twice using diisopropylcarbodiimide/1-hydroxybenzotriazole for 60 min. Fmoc deprotection was carried out using a mixture of 2% (v/v) piperidine and 2% (v/v) 1,8-diazabicyclo-[5.4.0]undec-7-ene in dimethylformamide followed by treatment with 25% piperidine in dimethylformamide. Side chains were protected with the following groups: t-butyl (Glu, Ser, and hydroxy-Pro), 2,2,5,7,8-pentamethylchroman-6-sulfonyl (Arg), and trityl (Gln).

After the completion of synthesis, peptide resins were washed thoroughly with dimethylformamide, ethanol, and ether and then dried in a vacuum desiccator. Peptides were released from the resin by treatment with a mixture of trifluoroacetic acid, thioanisole, ethanedithiol, and triethylsilane (90:5:2.5:2.5 by volume) for 8 h. The resins were filtered, and the peptides were precipitated with cold anhydrous ether. The precipitate was washed with anhydrous ether three times and dried. The cleaved peptides were analyzed by reverse phase high pressure liquid chromatography on a Waters 625 liquid chromatography system (Milford, Mass.) using a Waters Delta-Pak C18 column.

EXAMPLE 7

Circular Dichroism (CD) Spectroscopy

Synthetic collagen peptides were analyzed by CD spectroscopy, as described previously (Xu, Y. et al., 2000) with the following modifications. Briefly, peptides were dissolved in HBS to a concentration of 50 μM. CD spectra were collected on a Jasco J720 spectropolarimeter (Tokyo, Japan) from 190 to 240 nm, with bandwidth of 1 nm and integrated for 1 s at 0.2 nm intervals. Samples were measured at room temperature using cuvettes with 0.02 cm path length. For temperature-dependant denaturation analysis, 30 mM of peptides were added to a thermostatically controlled cuvette with a 0.5 cm path length. Thermal transition profiles were recorded at 225 nm as described above with a temperature slope of 20° C./hr. To calculate the temperature melting points, the thermal transition profiles were fitted with Boltzmann sigmoidal model using the GraphPad Prism™ software (GraphPad Software Inc., San Diego, Calif.).

EXAMPLE 8

Reagents and Cell Culture

The human recombinant mature type III collagen used for cell attachment assays was purchased from FibroGen. All cell culture media components were purchased from Invitrogen. The human lung fibroblast cell line MRC-5 was purchased from American Type Culture Collection (ATCC) (Manassas, Va.). The cells were cultured and passaged in Dulbecco's modified Eagle's medium (DMEM) supplemented with 10% fetal bovine serum, 100 unit/ml penicillin and 100 μg/ml streptomycin. The cells were grown to subconfluence and passaged every 2-3 days.

EXAMPLE 9

Cell Attachment Assay

MRC-5 cells were starved overnight in serum deficient DMEM containing penicillin and streptomycin, then detached using 1 mM EDTA and 0.025% trypsin at 37° C. for 2 minutes. The cells were washed with PBS and resuspended in DMEM containing 0.2% BSA supplemented with 2 mM MgCl2. 100 μl of the cell suspension (~1.5×10$^5$ cells/ml) were added to the microtiter wells coated with different concentrations of collagen or collagen peptides and blocked with PBS containing 0.5% (w/v) BSA. After incubation at room temperature for 45 min, the wells were washed with PBS. Attached cells were fixed with 3% p-formaldehyde for 10 min at room temperature. Following washing with cold Tris-buffered saline (TBS), pH 7.4, cells were fixed again in 20% methanol for 10 min and stained with 0.5% crystal violet for 5 min. The wells were thoroughly washed with distilled water and air-dried. Sodium citrate (0.1 M) was then added to the wells to dissolve the dye and the absorbance at 590 nm was measured. The maximum cell attachment on type III collagen was set to 100% and, residual attachment on BSA was set to 0%.

EXAMPLE 10

Computer Modeling

The coordinates of the crystal structure of $\alpha_2$I in complex with a synthetic collagen peptide were obtained from Protein Data Bank (code 1dzi) and used as a template for the model studies. First, the Phe residues in both the middle and trailing strands were replaced by Arg residues. Then local minimization was carried out in sizes of 5 Å for best fit. Several basic components (i.e., hydrogen bond, van der Waals and electrostatic interactions) contributing to the binding energy between $\alpha_2$I and the mutated collagen peptide were analyzed. The molecular modeling experiment was carried out under ECEPP/3 force field by using the ICM software (Molsoft, La Jolla, Calif.).

EXAMPLE 11

Characterization of the Binding of $\alpha_1$I and $\alpha_2$I to Type I, II and III Collagens The interactions between the two I domains and fibrillar collagens (types I, II and III) were examined by SPR. Solutions of 1 μM $\alpha_1$I or $\alpha_2$I were passed over chips containing immobilized collagen I, II, or III in the presence of 1 mM MgCl2. Both $\alpha_1$I and $\alpha_2$I showed binding to all three types of collagen (FIG. 1), consistent with previous reports (Nykvist, P et al., 2000). To determine the dissociation constants ($K_D$) for the interactions between the I domains and each collagen, increasing concentrations of recombinant I domains (0.01-50 μM) were passed over the collagen surfaces. In previous SPR studies using BIAcore 1000 system, two classes of binding sites in type I collagen having different affinities for $\alpha_1$I were shown ($K_{D1}$=0.26±0.01 mM, and $K_{D2}$=13.9±3.0 mM), whereas $\alpha_2$I appeared to have one class of binding sites (~10 mM) (Rich et al., 1999).

The BIAcore 3000 system used in the present invention had higher sensitivity of detection which enabled examination of the interactions between $\alpha_2$I and collagens at a sub-micromolar concentration range. Analyses using the SPR responses in the steady state portion of the sensorgrams, which indicates the equilibrium condition, showed that both I domains have at least two classes of binding sites in the three types of collagen. The dissociation constants ($K_D$) of these interactions are summarized in Table 2. $\alpha_1$I binds all three types of collagen with similar affinities ($K_{D1}$=~0.15–0.32 mM, and $K_{D2}$=~5.5–7.3 mM). The binding affinities of $\alpha_2$I to the three types of collagen appeared to be slightly more variable. The $K_D$ values for the high affinity binding class range from ~0.3 μM for types I and III collagen, to 1.75 μM for type II collagen, whereas the $K_D$ values for the low affinity binding class range from ~4 μM for type I collagen, to ~16.5 μM and ~14.5 μM for type II and III collagen, respectively.

The two recombinant I domains also exhibited different binding kinetics to the collagens as indicated by the shape of the corresponding SPR sensorgrams (FIG. 1). Comparison of the shapes of the SPR sensorgrams of $\alpha_1 I$ with those of $\alpha_2 I$ indicated a much slower association and dissociation rate of $\alpha_1 I$ compared to $\alpha_2 I$ in agreement with previous reports (Xu, Y et al., 2000; Rich, R. L. et al., 1999). However there was no dramatic difference between each I domain binding to type I, II and type III collagen. Thus, the binding characteristics of the interactions between $\alpha_1 I/\alpha_2 I$ and type III collagen are similar to those of the interactions between $\alpha_1 I/\alpha_2 I$ and type I/II collagen.

TABLE 2

Summary of the binding affinities of $\alpha_1 I$ and $\alpha_2 I$ to fibrillar collagens (types I–III)

| | $K_D{}^a$ | |
|---|---|---|
| | $\alpha_1 I$ | $\alpha_2 I$ |
| Collagen I | 0.32 ± 0.10 | 0.26 ± 0.08 |
| | 5.5 ± 1.46 | 3.99 ± 0.82 |
| Collagen II | 0.15 ± 0.03 | 1.75 ± 0.09 |
| | 7.28 ± 1.16 | 16.5 ± 3.89 |
| Collagen III | 0.19 ± 0.03 | 0.33 ± 0.03 |
| | 6.15 ± 0.95 | 14.5 ± 3.41 |

$^a$KD was calculated by equilibrium analysis. Data are presented as mean value ± S.E of three independent studies.

EXAMPLE 12

Localization of a High Affinity $\alpha_1 I$ and $\alpha_2 I$ Binding Region in Type III Procollagen Two sequence motifs, GFOGER and GLOGER, were identified as high affinity binding sites in triple helical collagen for $\alpha_1 I$, $\alpha_2 I$ and $\alpha_{11} I$ (Zhang, W. M. et al., 2003; Siljander, P. R. et al., 2004, Xu, Y et al., 2000). The fact that these sequences were present in type I and I collagen but not in type III collagen suggested the presence of at least one novel high affinity binding site in type III collagen. To locate the high affinity binding region(s) in type III collagen, collagen and I domain complexes were examined by rotary shadowing followed by electron microscopy (EM). Type III procollagen was used in these experiments since it contains a globular-shaped C-terminal propeptide that allows the determination of the orientation of collagen molecules in EM.

Type III procollagen was incubated with $\alpha_1 I$ or $\alpha_2 I$ under binding conditions and the complexes were then subjected to rotary shadowing and EM. The helical portion of the majority of the collagen molecules was found to be ~300 nm long, indicating that these molecules were mostly intact, full-length molecules. Multiple binding sites in the helical portion of type III collagen were observed for both $\alpha_1 I$ and $\alpha_2 I$ (FIG. 2), however, one region at 270-300 nm from the C-terminal end of the mature chain contained approximately 75% and 25% of the total binding events of $\alpha_1 I$ (n=269) and $\alpha_2 I$ (n=299), respectively (FIG. 3), suggesting that this region contained high affinity binding site(s) for $\alpha_1 I$ and $\alpha_2 I$. Furthermore, adding EDTA to the incubation buffer before the rotary shadowing dramatically reduced the number of I domains bound to procollagens, suggesting that this binding was metal ion dependent (data not shown).

EXAMPLE 13

Figures 4A, 4B, 4C:
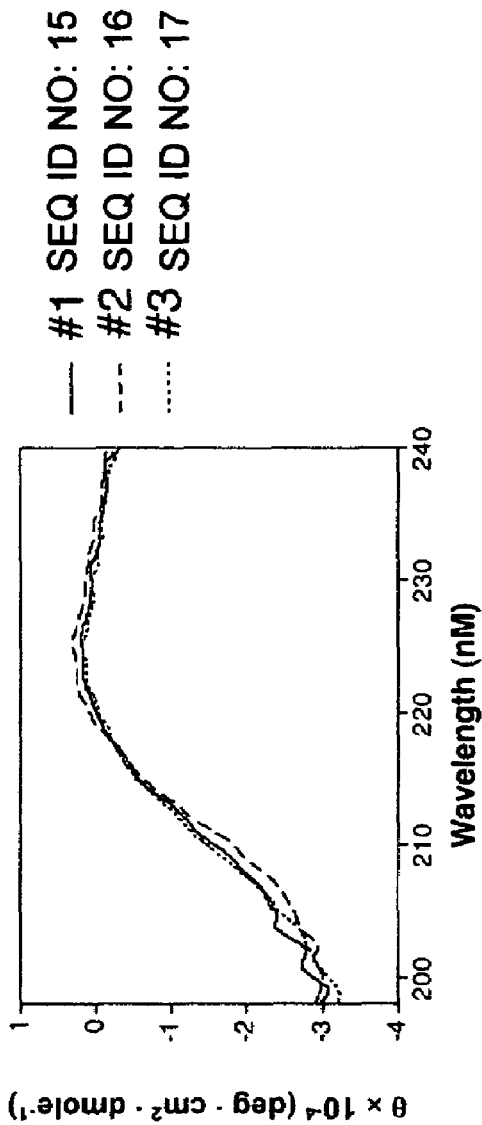
FIGS. 4A-C show collagen peptides from putative high affinity binding sequences in type III collagen.

Synthesis and Characterization of Collagen-Like Peptides Mimicking Putative High Affinity Binding Sites in Type III Collagen Type III collagen is a homotrimer composed of three $\alpha 1(III)$ polypeptides, each containing 1029 amino acid residues in the mature chain (GenBank™ accession number P02461). Given that the average collagen molecule measured 300 nm, the average length per residue of collagen was 0.29 nm (3.43 amino acid residues/nm), which was consistent with previous calculations (Bella et al., 1994). Based on this correlation, the region located 270-300 nm region from C-terminal end of the mature chain corresponded to amino acid residues 168-270 of the $\alpha 1(III)$ chain. This stretch of sequence contained one GER motif preceded by GROGRO (SEQ ID NO: 13) and followed by GLO (FIG. 4 A). If a GER sequence was critical for integrin binding, this collagen sequence was a potential high affinity site for $\alpha_1 I$ and $\alpha_2 I$. There was another GER motif preceded by GAO and followed by GROGLO (SEQ ID NO: 14) close to C-terminal side of the 270-300 nm region. Therefore, peptides $(GPO)_3$ $GROGROGERGLO(GPO)_3$ (peptide #1; SEQ ID NO: 15) and $(GPO)_3 GAOGERGROGLO(GPO)_3$ (peptide #2; SEQ ID NO: 16) were synthesized and used in I domain binding assays. Peptide $(GPO)_{11}$ (peptide #3; SEQ ID NO: 17), was used as a control peptide (FIG. 4B).

The synthetic peptides were examined for their ability to form collagen-like triple helices by CD spectroscopy. The CD spectra of all four peptides showed the characteristic ellipticity maxima at 220-225 nm, indicating that they were capable of forming collagen-like triple helices (FIG. 4C). The temperature-dependent unfolding of the triple helix was followed by monitoring the CD at 225 nm. The reduction of the maxima was seen from about 35° C.-with melting points for the triple helix structure of these peptides recorded between 41 and 44° C. (data for peptide #1 are shown in FIG. 8B). The data discussed herein showed that the peptides formed triple helix structure at temperatures (4-25° C.) used in the following experiments.

EXAMPLE 14

Figure 5A:
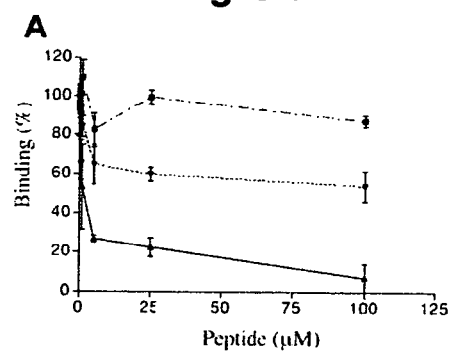
FIGS. 5A-D show inhibition of the binding of $\alpha_1 I$ and $\alpha_2 I$ to collagens by synthetic collagen peptides. Different concentrations of peptides (0.01-100 µM) were mixed with 0.5 µM $\alpha_1 I$ (FIGS. 5A, 5C) and 5 µM $\alpha_2 I$ (FIGS. 5B, 5D) before being added to microtiter wells coated with type III procollagen (FIGS. 5A, 5B) or type I collagen (FIGS. 5C, 5D). Bound $\alpha_1 I$ or $\alpha_2 I$ were detected by anti-His monoclonal antibody, followed by goat anti-mouse IgG (H+L)-alkaline phosphatase conjugate. The binding in the absence of peptide was set to 100%. Data were presented as the mean value±S.E. of A405 nm (n=3) from a representative experiment. Peptides #1, #2 and #3 in these figures are identified as SEQ ID NO: 15, 16 and 17, respectively.
Figure 5B:
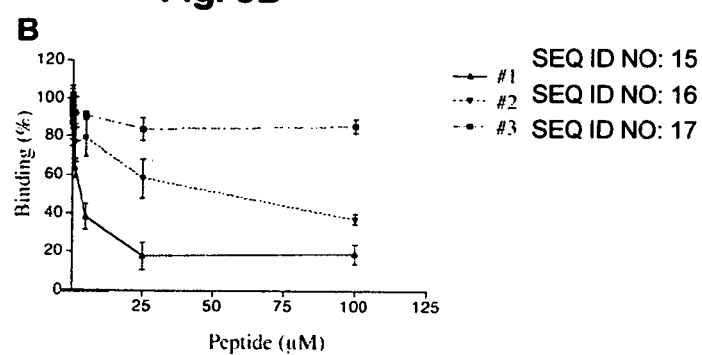
Figure 5C:
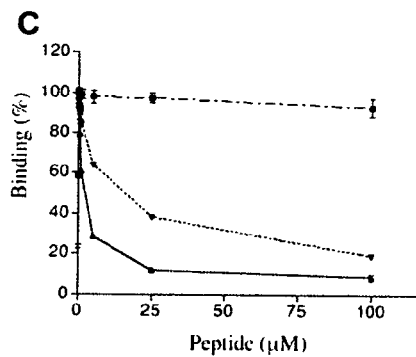
Figure 5D:
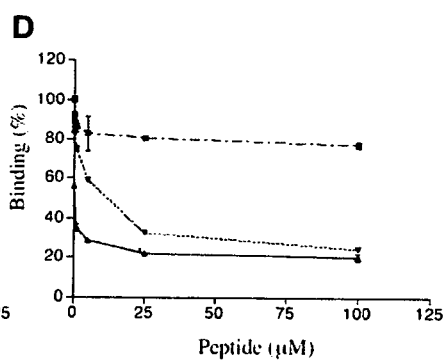

Inhibition of $\alpha_1 I$ and $\alpha_2 I$ Binding to Type I and Type III Collagen by Synthetic Collagen Peptides To determine whether the type III collagen peptides contained high affinity binding sites for $\alpha_1 I$ and $\alpha_2 I$, their ability to inhibit the binding of recombinant I domains to type I and III collagens was examined using ELISAs type assays. Various concentrations of peptides (0.01-100 µM) were incubated with recombinant I domains before the mixtures were added to microtiter wells coated with type I or III collagen. The results indicated that at 100 µM, peptide #1 (SEQ ID NO: 15) inhibited the binding of $\alpha_1 I$ and $\alpha_2 I$ to type III collagen by 100% and 80%, respectively (FIGS. 5A and B). Peptide #2 (SEQ ID NO: 16) at 100 µM inhibited the binding of $\alpha_1 I$ and $\alpha_2 I$ to type III collagen by 40% and 60% respectively, suggesting that although peptide #2 (SEQ ID NO: 16) was recognized by the I domains, it was not a high affinity binding site. The control peptide #3 (SEQ ID NO: 17) did not show any inhibitory activity. The $IC_{50}$ values of peptide #1 (SEQ ID NO: 15) with $\alpha_1 I$ and $\alpha_2 I$ binding to type III collagen were 1.0±0.6 µM and 1.9±0.9 µM, respectively. Similar results were obtained with type I collagen; the $IC_{50}$ values of peptide #1 (SEQ ID NO: 15) with $\alpha_1 I$ and $\alpha_2 I$ binding to type I collagen were 1.4±0.4 µM and 0.14±0.09 µM, respectively (FIGS. 5C and D).

EXAMPLE 15

Characterization of the Binding of I Domains to Collagen Peptide #1

Figure 6A:
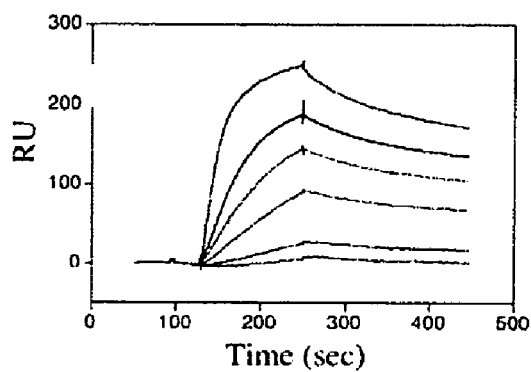
FIGS. 6A-C show representative SPR sensorgrams of $\alpha_1 I$ and $\alpha_2 I$ binding to immobilized peptide #1 (SEQ ID NO: 15). Increasing concentrations (0.5, 1, 3, 6, 10 and 30 nM) of $\alpha_1 I$ (FIG. 6A) or $\alpha_2 I$ (FIG. 6B), were passed over a surface containing synthetic peptide #1 (SEQ ID NO: 15). Responses to blank cells were subtracted. The binding was abolished in the presence of 2 mM EDTA (FIG. 6C).
Figure 6B:
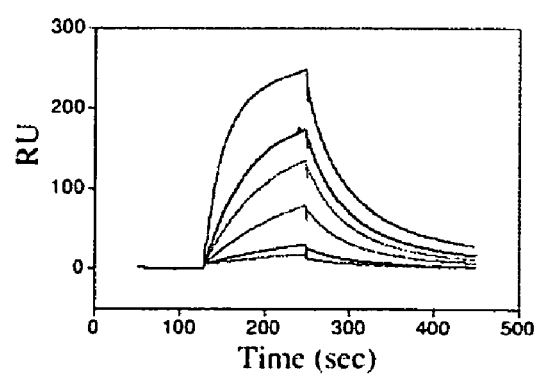
Figure 6C:
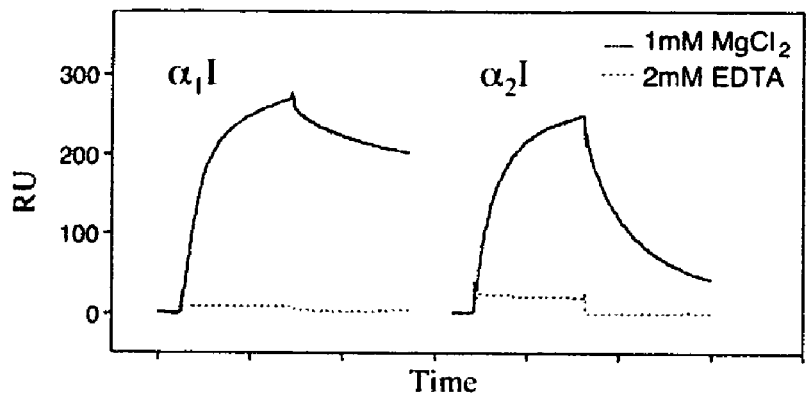

The direct binding of the $\alpha_1 I$ and $\alpha_2 I$ domains to peptide #1 was investigated further using SPR. Peptide #1 (SEQ ID NO: 15) was immobilized onto a CM5 chip. Increasing concentrations of I domains (0.5-30 nM) were passed over the surface containing peptide #1 (SEQ ID NO: 15). $\alpha_1 I$ and $\alpha_2 I$ exhibited similar association rates for peptide #1, 5.6 $Ms^{-1} \times 10^4$ and 4.4 $Ms^{-1} \times 10^4$, respectively, however, $\alpha_1 I$ showed a much slower dissociate rate than $\alpha_2 I$, 1.3 $s^{-1} \times 10^3$ compared to 12 $s^{-1} \times 10^3$ for $\alpha_2 I$ (FIGS. 6A and B, and Table 3). This resulted in a $K_D$ of 23 nM for the interactions between $\alpha_1 I$ and peptide #1 (SEQ ID NO: 15), and a $K_D$ of 283 nM for the interactions between $\alpha_2 I$ and peptide #1 (SEQ ID NO: 15) (Table 3). To test whether the binding of $\alpha_1 I$ and $\alpha_2 I$ to peptide #1 (SEQ ID NO: 15) was metal ion dependent, 30 nM of each I domain in the presence of either 1 mM MgCl2 or 2 mM EDTA was passed over a peptide #1 (SEQ ID NO: 15)-coated surface. The presence of EDTA completely abolished binding, indicating that the interactions were dependent on the presence of divalent cations (FIG. 6C).

TABLE 3

Analyses of the binding of $\alpha_1 I$ and $\alpha_2 I$ to synthetic collagen peptide #1 (SEQ ID NO: 15).

| | $k_{on}(MS^{-1}(\times 10^4))$ | $k_{off}(S^{-1}(\times 10^{-3}))$ | $k_D(nM)$ |
|---|---|---|---|
| $\alpha_1 I$ | 5.6 | 1.3 | 23 |
| $\alpha_2 I$ | 4.4 | 12 | 283 |

EXAMPLE 16

Adhesion of MRC-5 Cells to Peptide #1 (SEQ ID NO: 15) Substrates

Figure 7:
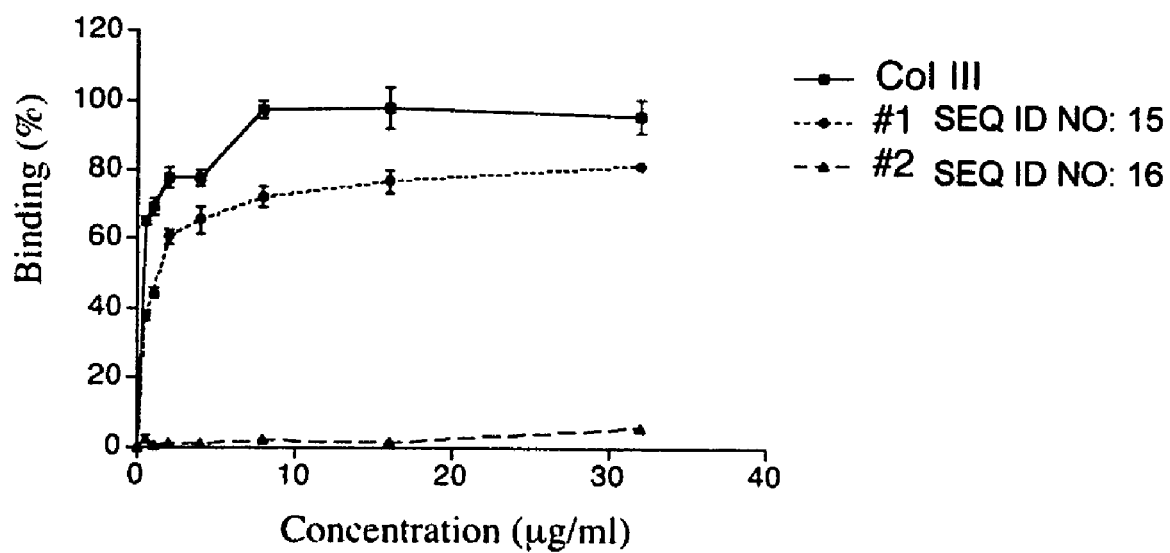
FIG. 7 shows adhesion of MRC-5 cells to synthetic collagen peptides. Microtiter wells were coated with increasing concentrations of type III collagen or collagen peptides (SEQ ID NO: 15 or SEQ ID NO: 16). Both peptides were present in a triple helix conformation and immobilized to similar extent in the wells as tested by the amount of recombinant CAN bound to the two substrates (data not shown). Approximately $1.5 \times 10^4$ cells were added to the wells and allowed to adhere to the substrates at room temperature for 45 min. Bound cells were fixed and then detected with crystal violet.
Figure 9A:
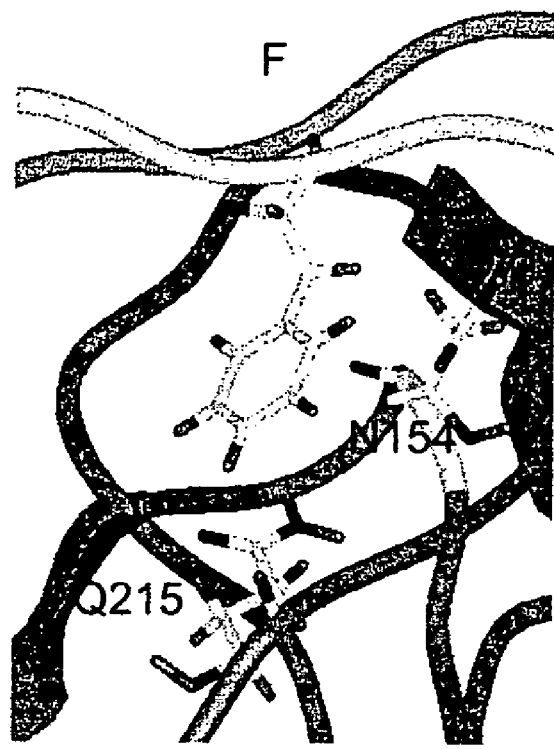
FIGS. 9A-D show computer modeling of the interactions between $\alpha_2 I$ and synthetic collagen peptide #1 (SEQ ID NO: 15). The trailing and middle strands of the collagen peptide and the backbones of $\alpha_2 I$ are presented in green, yellow, and grey, respectively. All residues displayed are shown with oxygen in red, nitrogen in blue and carbon in white, green or yellow for residues from $\alpha_2 I$, the trailing and the middle strand of collagen, respectively. The interactions between $Asn^{154}$ and $Gln^{215}$ of $\alpha_2 I$ and the middle strand of the collagen peptide GFOGER (SEQ ID NO: 1) (FIG. 9A) and GROGER (SEQ ID NO: 4) (FIG. 9B), and $Leu^{286}$ and $Tyr^{157}$ of $\alpha_2 I$ and the trailing strand of GFOGER (SEQ ID NO: 1) (FIG. 9C) and GROGER (SEQ ID NO: 4) (FIG. 9D) are shown.
Figure 9B:
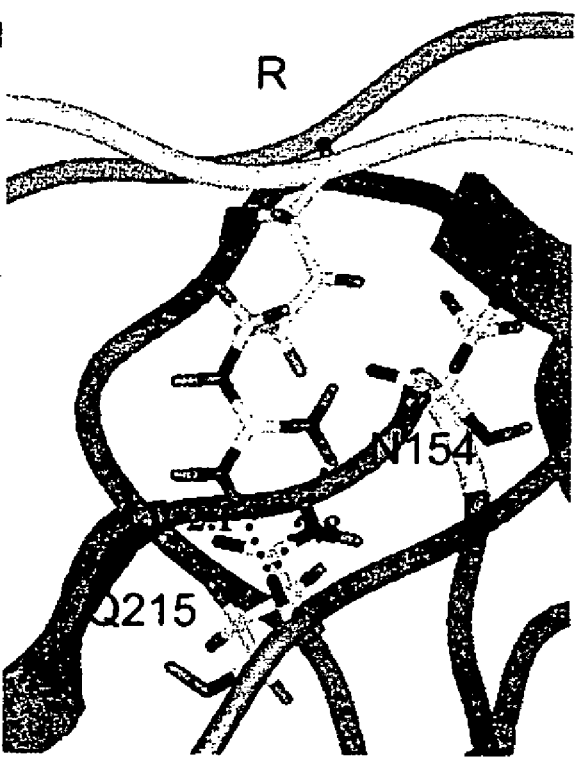
Figure 9C:
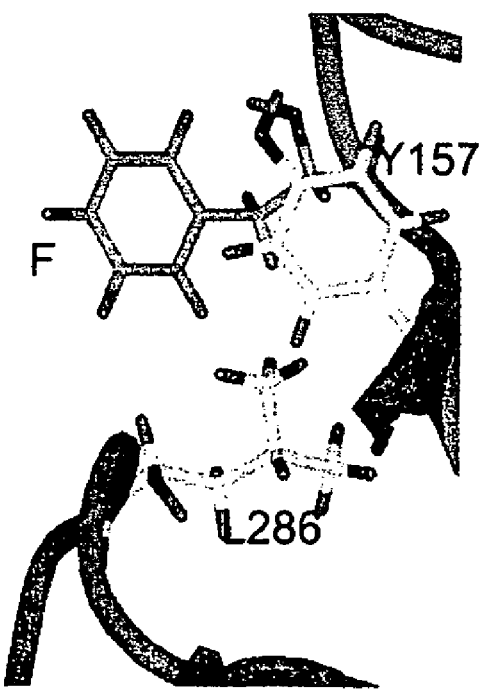
Figure 9D:
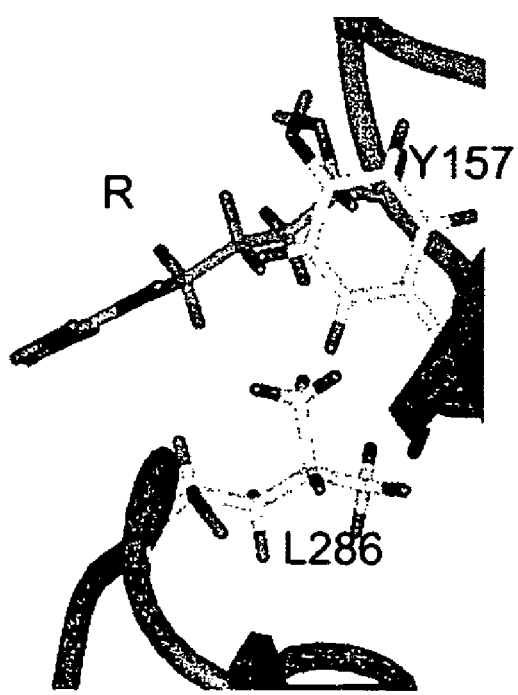

In order to investigate whether the synthetic collagen peptide #1 (SEQ ID NO: 15) was able to support cell adhesion, the human lung fibroblast cell line, MRC-5, which was shown previously to express comparable levels of $\alpha_1\beta_1$ and $\alpha_2\beta_1$ integrins (Humtsoe et al., 2005) was used. Wells in 96-well plates were coated with increasing concentrations of type III collagen, peptide #1 (SEQ ID NO: 15) or #2 (SEQ ID NO: 16) and 1.5×10⁴ MRC-5 cells were added to each well. The plate was incubated for 45 min at room temperature and adhering cells were quantified as described herein. The results showed that peptide #1 (SEQ ID NO: 15) and type III collagen could support adhesion of MRC-5 cells in a dose-dependent manner, whereas peptide #2 (SEQ ID NO: 16) could not (FIG. 7). Considerable cell spreading was observed among cells incubated on peptides #1 (SEQ ID NO: 15) at room temperature for 1.5 hrs similar to cells seeded on type III collagen (data not shown).

EXAMPLE 17

GROGER (SEQ ID NO: 4) is a Minimal $\alpha_1 I/\alpha_2 I$ High Affinity Binding Motif To determine the minimal binding sequence in peptide #1 (SEQ ID NO: 15), a shorter peptide containing the GROGER (SEQ ID NO: 4) sequence flanked by three GPO repeats at either ends was synthesized. Peptides containing GFOGER (SEQ ID NO: 1) and GLOGER (SEQ ID NO: 2) motifs were also made for comparison (FIG. 8A). All three peptide were able to form triple helices as shown by their ellipticity maxima around 225 nm in the CD spectra (data not shown). In addition, all three showed a sharp decrease in their ellipticity at 225 nm as temperature increased. The melting temperature (Tm) of the GFOGER (SEQ ID NO: 1), GLOGER (SEQ ID NO: 2) and GROGER (SEQ ID NO: 4) peptides were determined to be between 37° C. and 41° C. The denaturation profile of GROGER (SEQ ID NO: 4) peptide was compared to that of the peptide #1 (SEQ ID NO: 15). The Tm of the GROGER (SEQ ID NO: 4) peptide was 41° C., slightly lower than the Tm of peptide #1 (SEQ ID NO: 15) which was determined to 43° C. (FIG. 8B).

To test whether GROGER (SEQ ID NO: 4) represented a high affinity binding site for $\alpha_1 I$ and $\alpha_2 I$, ability of the three peptides to inhibit the binding of the two I domains was compared to type III collagen using competition ELISAs. In these experiments, recombinant human mature type III collagen from FibroGen was used instead of procollagen III and peptide #1 was used due to the limited availability of the later. The recombinant I domains bound mature type III collagen in a similar way as to type III procollagen (data not shown). The results showed that GROGER (SEQ ID NO: 4), as well as GFOGER (SEQ ID NO: 1) and GLOGER (SEQ ID NO: 2), inhibited the binding of $\alpha_1 I$ and $\alpha_2 I$ to the immobilized collagen (FIGS. 8C and D). The $IC_{50}$ values of GFOGER (SEQ ID NO: 1), GLOGER (SEQ ID NO: 2) and GROGER (SEQ ID NO: 4) were 1.9±0.03 µM, 2.2±0.01 µM and 3.6±0.09 µM respectively and, for the inhibition of $\alpha_2 I$ binding were 1.4±0.1 µM, 12.0±1.1 µM and 1.1±0.04 µM, respectively. In addition, the $IC_{50}$ values determined for GROGER (SEQ ID NO: 4) were in the same range as those for the peptide #1, which was used as positive control in this experiment. Thus, GROGER (SEQ ID NO: 4) represented a minimal high affinity binding sequence for $\alpha_1 I$ and $\alpha_2 I$.

EXAMPLE 18

Molecular Modeling of the Interactions Between GROGER (SEQ ID NO: 4) and $\alpha_2 I$ The crystal structure of $\alpha_2 I$ in complex with a synthetic collagen peptide containing the sequence GFOGER (SEQ ID NO: 1) has been reported (Emsley, J. et al., 2000). The structure shows that the Glu residue directly interacted with the divalent cation $Mg^{2+}$ co-ordinated by the MIDAS motif found in the $\alpha_2 I$. Another high affinity binding site composed of the sequence GLOGER (SEQ ID NO: 2) also contains a hydrophobic residue at the second position. However, the present invention reported an integrin-binding sequence GROGER (SEQ ID NO: 4) that contained a charged Arg residue at the second position. In order to examine how the $\alpha_2 I$ structure accommodated this charged residue, in place of a hydrophobic residue, computer modeling was performed. In the published $\alpha_2 I$-GFOGER (SEQ ID NO: 1) complex structure (PDB code 1dzi), Phe in the middle strand of the collagen triple helix participated in van der Waals interactions with the side chains of $Asn^{154}$ and $Gln^{215}$ of $\alpha_2 I$ and Phe in the trailing strand participated in van der Waals contacts with Leu[286] and Tyr[157] of $\alpha_2$I (Emsley, J et al., 2000). Replacing Phe with Arg in the collagen peptide did not change the positions of neighboring residues in $\alpha_2$I. In the analysis of the molecular interactions between specific residues of $\alpha_2$I and Arg in both middle and trailing strands, the modified complex retained the van der Waals interactions previously described in the interaction with Phe (FIG. 9). Furthermore, a new hydrogen bond interaction was observed between the carbonyl backbone of $Gln_{215}$ of $\alpha_2$I and the Arg residue in the middle strand with a distance of 2.1 Å (FIG. 9, B). Thus, it appeared that the second position in the collagen peptide sequence was tolerant to substitutions, and that GROGER (SEQ ID NO: 4) represented a novel binding motif for the collagen-binding I domains.

EXAMPLE 19

Computer-Aided Molecular Modeling to Identify Integrin Specific Inhibitors

As discussed earlier, the interaction between integrin and collagen is mediated by the I domain present in the α chain of the integrin. The crystal structure of the $\alpha_2$I domain in complex with a collagen triple helix peptide showed that GFOGER (SEQ ID NO: 1) represented a binding site for $\alpha_2$I in collagen. Similarly, GLOGER (SEQ ID NO: 2) was recognised by $\alpha_2$I as well as by $\alpha_1$I, $\alpha_{11}$I.

Molecular modeling approach was used to define all binding sequences in collagen. It was observed that the integrin domains could bind to a number of sites in collagen. It is contemplated that some of the sites are recognized by all integrins whereas others are specifically recognized by individual I-domains (FIGS. 10A-D). Thus, these specific sequences provide a base for developing integrin specific inhibitors.

The following references were cited herein:
Bella, J et al., 1994, *Science* 266: 75-81.
Camper, L., et al., 1998, *J Biol Chem* 273: 20383-20389
Emsley J, et al., 2000, *Cell* 101: 47-56.
Gelse, K. et al., 2003, Adv Drug Deliv Rev, 55: 1531-1546.
Gullberg, D. E. and Lundgren-Akerlund, E., 2002, *Prog Histochem Cytochem* 37: 3-54.
Hulmes, D. J., 1992, Essays Biochem, 27: 49-67.
Humtsoe, J. O., et al., 2005 *J Biol Chem*, 280: 13848-13857.
Hynes, R. O., 1992, Cell, 69: 11-25.
Knight, C. G., et al., 1998, *J Biol Chem* 273: 33287-33294
Knight, C. G., et al. 2000, *Journal of Biological Chemistry* 275: 35-40
Kramer, R. H. and Marks, N., 1989, J Biol Chem, 264: 4684-4688.
Kuivaniemi, H. et al., 1997, Hum Mutat, 9: 300-315.
Lee, J. O., et al. 1995, *Structure* 3, 1333-1340
Liu, X., et al., 1997, *Proc Natl Acad Sci USA* 94: 1852-1856
Myllyharju, J and Kivirikko, K. I., 2001, Ann Med, 33: 7-21.
Nykvist, P., et al., 2000 *J Biol Chem* 275: 8255-8261.
Patti, J. M. et al., 1992, *J Biol Chem* 267: 4766-4772.
Prockop, D. J and Kivirikko, K. I., 1995, Annu Rev Biochem 64:403-434.
Ramchandran, G. N. 1988, Int J Pept Protein Res., 31: 1-16.
Rich, R. L., et al. 1999, *J Biol Chem* 274: 24906-24913
Siljander, P. R., et al., 2000, *Cell* 101: 47-56.
Velling, T. et al., 1999, *J Biol Chem* 274: 2573525742
Xu, Y., et al., 2000, *J Biol Chem* 275: 38981-38989.
Zhang, W. M., et al., 2003, *J Biol Chem* 278: 7270-7277

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

SEQUENCE LISTING

<160> NUMBER OF SEQ ID NOS: 21

<210> SEQ ID NO 1
<211> LENGTH: 6
<212> TYPE: PRT
<213> ORGANISM: Unknown
<220> FEATURE:
<221> NAME/KEY: CHAIN
<222> LOCATION: 3
<223> OTHER INFORMATION: collagen-derived sequence that binds integrins;
      Xaa at position 3 is hydroxyproline

<400> SEQUENCE: 1

Gly Phe Xaa Gly Glu Arg
              5

<210> SEQ ID NO 2
<211> LENGTH: 6
<212> TYPE: PRT
<213> ORGANISM: Unknown
<220> FEATURE:
<221> NAME/KEY: CHAIN
<222> LOCATION: 3
<223> OTHER INFORMATION: collagen-derived sequence that binds integrins;

```
      Xaa at position 3 is hydroxyproline

<400> SEQUENCE: 2

Gly Leu Xaa Gly Glu Arg
                5

<210> SEQ ID NO 3
<211> LENGTH: 6
<212> TYPE: PRT
<213> ORGANISM: Unknown
<220> FEATURE:
<221> NAME/KEY: CHAIN
<223> OTHER INFORMATION: collagen-derived sequence that binds integrins

<400> SEQUENCE: 3

Gly Ala Ser Gly Glu Arg
                5

<210> SEQ ID NO 4
<211> LENGTH: 6
<212> TYPE: PRT
<213> ORGANISM: Unknown
<220> FEATURE:
<221> NAME/KEY: CHAIN
<222> LOCATION: 3
<223> OTHER INFORMATION: binding motif for collagen-binding integrin
      domain; Xaa at position 3 is hydroxyproline

<400> SEQUENCE: 4

Gly Arg Xaa Gly Glu Arg
                5

<210> SEQ ID NO 5
<211> LENGTH: 6
<212> TYPE: PRT
<213> ORGANISM: Unknown
<220> FEATURE:
<221> NAME/KEY: CHAIN
<222> LOCATION: 3
<223> OTHER INFORMATION: collagen-derived sequence that binds integrins;
      Xaa at position 3 is hydroxyproline.

<400> SEQUENCE: 5

Gly Ala Xaa Gly Glu Arg
                5

<210> SEQ ID NO 6
<211> LENGTH: 6
<212> TYPE: PRT
<213> ORGANISM: Artificial sequence
<220> FEATURE:
<221> NAME/KEY: CHAIN
<223> OTHER INFORMATION: sequence of an inhibitor of collagen-integrin
      binding

<400> SEQUENCE: 6

Gly Phe Pro Gly Glu Arg
                5

<210> SEQ ID NO 7
<211> LENGTH: 6
<212> TYPE: PRT
<213> ORGANISM: Artificial sequence
<220> FEATURE:
<221> NAME/KEY: CHAIN
<222> LOCATION: 3
<223> OTHER INFORMATION: sequence of an inhibitor of collagen-integrin
      binding; Xaa at position 3 is hydroxyproline
```

```
<400> SEQUENCE: 7

Gly Phe Xaa Gly Glu Asn
              5

<210> SEQ ID NO 8
<211> LENGTH: 6
<212> TYPE: PRT
<213> ORGANISM: Artificial sequence
<220> FEATURE:
<221> NAME/KEY: CHAIN
<222> LOCATION: 3
<223> OTHER INFORMATION: sequence of an inhibitor of collagen-integrin
      binding; Xaa at position 3 is hydroxyproline

<400> SEQUENCE: 8

Gly Phe Xaa Gly Glu Lys
              5

<210> SEQ ID NO 9
<211> LENGTH: 6
<212> TYPE: PRT
<213> ORGANISM: Artificial sequence
<220> FEATURE:
<221> NAME/KEY: CHAIN
<222> LOCATION: 3
<223> OTHER INFORMATION: sequence of an inhibitor of collagen-integrin
      binding; Xaa at position 3 is hydroxyproline

<400> SEQUENCE: 9

Gly Asn Xaa Gly Glu Arg
              5

<210> SEQ ID NO 10
<211> LENGTH: 6
<212> TYPE: PRT
<213> ORGANISM: Artificial sequence
<220> FEATURE:
<221> NAME/KEY: CHAIN
<222> LOCATION: 3
<223> OTHER INFORMATION: sequence of an inhibitor of collagen-integrin
      binding; Xaa at position 3 is hydroxyproline

<400> SEQUENCE: 10

Gly Ser Xaa Gly Glu Arg
              5

<210> SEQ ID NO 11
<211> LENGTH: 6
<212> TYPE: PRT
<213> ORGANISM: Artificial sequence
<220> FEATURE:
<221> NAME/KEY: CHAIN
<222> LOCATION: 3
<223> OTHER INFORMATION: sequence of an inhibitor of collagen-integrin
      binding; Xaa at position 3 is hydroxyproline

<400> SEQUENCE: 11

Gly Val Xaa Gly Glu Arg
              5

<210> SEQ ID NO 12
<211> LENGTH: 6
<212> TYPE: PRT
<213> ORGANISM: Artificial sequence
<220> FEATURE:
<221> NAME/KEY: CHAIN
<222> LOCATION: 3
<223> OTHER INFORMATION: sequence of an inhibitor of collagen-integrin
      binding; Xaa is hydroxyproline
```

```
<400> SEQUENCE: 12

Gly Pro Xaa Gly Glu Arg
                5

<210> SEQ ID NO 13
<211> LENGTH: 6
<212> TYPE: PRT
<213> ORGANISM: Unknown
<220> FEATURE:
<221> NAME/KEY: CHAIN
<222> LOCATION: 3,6
<223> OTHER INFORMATION: sequence preceding the Gly-Glu-Arg motif of
      type III collagen; Xaa at positions 3 and 6
      is hydroxyproline

<400> SEQUENCE: 13

Gly Arg Xaa Gly Arg Xaa
                5

<210> SEQ ID NO 14
<211> LENGTH: 6
<212> TYPE: PRT
<213> ORGANISM: Unknown
<220> FEATURE:
<221> NAME/KEY: CHAIN
<222> LOCATION: 3,6
<223> OTHER INFORMATION: sequence following the Gly-Glu-Arg motif of
      type III collagen; Xaa at positions 3 and 6
      is hydroxyproline

<400> SEQUENCE: 14

Gly Arg Xaa Gly Leu Xaa
                5

<210> SEQ ID NO 15
<211> LENGTH: 30
<212> TYPE: PRT
<213> ORGANISM: Artificial sequence
<220> FEATURE:
<221> NAME/KEY: CHAIN
<222> LOCATION: 3,6,9,12,15,21,24,27,30
<223> OTHER INFORMATION: sequence within C-terminal end of collagen
      alpha 1(III) chain containing Gly-Glu-Arg motif; Xaa at
      positions 3, 6, 9, 12, 15, 21, 24, 27, 30 is
      hydroxyproline

<400> SEQUENCE: 15

Gly Pro Xaa Gly Pro Xaa Gly Pro Xaa Gly Arg Xaa Gly Arg Xaa
                5                  10                  15

Gly Glu Arg Gly Leu Xaa Gly Pro Xaa Gly Pro Xaa Gly Pro Xaa
                20                  25                  30

<210> SEQ ID NO 16
<211> LENGTH: 30
<212> TYPE: PRT
<213> ORGANISM: Artificial sequence
<220> FEATURE:
<221> NAME/KEY: CHAIN
<222> LOCATION: 3,6,9,12,18,21,24,27,30
<223> OTHER INFORMATION: sequence within C-terminal end of collagen
      alpha 1(III) chain containing Gly-Glu-Arg motif; Xaa at positions
      3, 6, 9, 12, 18, 21, 24, 27, 30 is hydroxyproline

<400> SEQUENCE: 16

Gly Pro Xaa Gly Pro Xaa Gly Pro Xaa Gly Ala Xaa Gly Glu Arg
                5                  10                  15

Gly Arg Xaa Gly Leu Xaa Gly Pro Xaa Gly Pro Xaa Gly Pro Xaa
```

```
                                         20                 25                  30

<210> SEQ ID NO 17
<211> LENGTH: 33
<212> TYPE: PRT
<213> ORGANISM: Artificial sequence
<220> FEATURE:
<221> NAME/KEY: CHAIN
<222> LOCATION: 3,6,9,12,15,18,21,24,27,30,33
<223> OTHER INFORMATION: synthetic control peptide comprising only the
      Gly-Pro-Xaa sequence; Xaa at positions 3, 6, 9,
      12, 15, 18, 21, 24, 27,30, 33 is hydroxyproline

<400> SEQUENCE: 17

Gly Pro Xaa Gly Pro Xaa Gly Pro Xaa Gly Pro Xaa Gly Pro Xaa
                 5                  10                  15

Gly Pro Xaa Gly Pro Xaa Gly Pro Xaa Gly Pro Xaa Gly Pro Xaa
                 20                 25                  30

Gly Pro Xaa

<210> SEQ ID NO 18
<211> LENGTH: 157
<212> TYPE: PRT
<213> ORGANISM: Unknown
<220> FEATURE:
<221> NAME/KEY: CHAIN
<222> LOCATION: 19,22,25,31,37,43,46,55,58,76,79,85,88,97,130,
      121, 136,145,151,154
<223> OTHER INFORMATION: residues 161-307 of collagen(III) binding
      region;Xaa at positions 19, 22, 25, 31, 37,
      43, 46, 55, 58, 76, 79, 85, 88, 97, 121, 130,
      136, 145, 151, 154 is hydroxyproline

<400> SEQUENCE: 18

Lys Ser Gly Val Ala Val Gly Gly Leu Ala Gly Tyr Pro Gly Pro
                 5                  10                  15

Ala Gly Pro Xaa Gly Pro Xaa Gly Pro Xaa Gly Thr Ser Gly His
                 20                 25                  30

Xaa Gly Ser Pro Gly Ser Xaa Gly Tyr Gln Gly Pro Xaa Gly Glu
                 35                 40                  45

Xaa Gly Gln Ala Gly Pro Ser Gly Pro Xaa Gly Pro Xaa Gly Ala
                 50                 55                  60

Ile Gly Pro Ser Gly Pro Ala Gly Lys Asp Gly Glu Ser Gly Arg
                 65                 70                  75

Xaa Gly Arg Xaa Gly Glu Arg Gly Leu Xaa Gly Pro Xaa Gly Ile
                 80                 85                  90

Lys Gly Pro Ala Gly Ile Xaa Gly Phe Pro Gly Met Lys Gly His
                 95                 100                 105

Arg Gly Phe Asp Gly Arg Asn Gly Glu Lys Gly Glu Thr Gly Ala
                 110                115                 120

Xaa Gly Leu Lys Gly Glu Asn Gly Leu Xaa Gly Glu Asn Gly Ala
                 125                130                 135

Xaa Gly Pro Met Gly Pro Arg Gly Ala Xaa Gly Glu Arg Gly Arg
                 140                145                 150

Xaa Gly Leu Xaa Gly Ala Ala
                 155

<210> SEQ ID NO 19
<211> LENGTH: 24
<212> TYPE: PRT
<213> ORGANISM: Artificial sequence
<220> FEATURE:
```

```
<221> NAME/KEY: CHAIN
<222> LOCATION: 3,6,9,12,18,21,24
<223> OTHER INFORMATION: synthetic collagen peptide; Xaa at positions 3,
      6, 9, 12, 18, 21, 24 is hydroxyproline

<400> SEQUENCE: 19

Gly Pro Xaa Gly Pro Xaa Gly Pro Xaa Gly Phe Xaa Gly Glu Arg
                5                   10                  15

Gly Pro Xaa Gly Pro Xaa Gly Pro Xaa
                20

<210> SEQ ID NO 20
<211> LENGTH: 24
<212> TYPE: PRT
<213> ORGANISM: Artificial sequence
<220> FEATURE:
<221> NAME/KEY: CHAIN
<222> LOCATION: 3,6,9,12,18,21,24
<223> OTHER INFORMATION: synthetic collagen peptide; Xaa at positions 3,
      6, 9, 12, 18, 21, 24 is hydroxyproline

<400> SEQUENCE: 20

Gly Pro Xaa Gly Pro Xaa Gly Pro Xaa Gly Leu Xaa Gly Glu Arg
                5                   10                  15

Gly Pro Xaa Gly Pro Xaa Gly Pro Xaa
                20

<210> SEQ ID NO 21
<211> LENGTH: 24
<212> TYPE: PRT
<213> ORGANISM: Artificial sequence
<220> FEATURE:
<221> NAME/KEY: CHAIN
<222> LOCATION: 3,6,9,12,18,21,24
<223> OTHER INFORMATION: synthetic collagen peptide; Xaa at positions 3,
      6, 9, 12, 18, 21, 24 is hydroxyproline.

<400> SEQUENCE: 21

Gly Pro Xaa Gly Pro Xaa Gly Pro Xaa Gly Arg Xaa Gly Glu Arg
                5                   10                  15

Gly Pro Xaa Gly Pro Xaa Gly Pro Xaa
                20
??
??
??
??
```

What is claimed is:

1. A synthetic collagen-like peptide that is the sequence of SEQ ID NO: 15; wherein amino acid Xaa in the sequence is hydroxyproline.

2. The synthetic peptide of claim 1, wherein the peptide has a triple helical structure.

3. The synthetic peptide of claim 1, wherein said peptide binds I domains of integrins α1 and α2.

4. The synthetic peptide of claim 1, wherein the peptides contain a binding motif for collagen-binding I domains that is amino acid sequence SEQ ID NO: 4.

5. The synthetic peptide of claim 4, wherein the motif is present on an N-terminus of human type III collagen or in the α1 and α2 chain of human type 1 collagen.

* * * * *